US009782359B2

(12) United States Patent
Oksche et al.

(10) Patent No.: US 9,782,359 B2
(45) Date of Patent: Oct. 10, 2017

(54) OPIOID COMPOSITION FOR TREATING SKIN LESIONS

(75) Inventors: Alexander Oksche, Limburg (DE); Kevin J. Smith, Cambridgeshire (GB); Derek Prater, Cambridgeshire (GB); Malcolm Walden, Cambridgeshire (GB); Will Heath, Cambridgeshire (GB); Bernard Kennedy, Dublin (IE); Vanessa Addison, Suffolk (GB); Hassan Mohammad, Cambridgeshire (GB)

(73) Assignee: EURO-CELTIQUE S.A., Luxembourg (LU)

( * ) Notice: Subject to any disclaimer, the term of this patent is extended or adjusted under 35 U.S.C. 154(b) by 0 days.

(21) Appl. No.: 12/991,338

(22) PCT Filed: May 5, 2009
(Under 37 CFR 1.47)

(86) PCT No.: PCT/EP2009/055422
§ 371 (c)(1),
(2), (4) Date: Sep. 19, 2011

(87) PCT Pub. No.: WO2009/135846
PCT Pub. Date: Nov. 12, 2009

(65) Prior Publication Data
US 2012/0093929 A1 Apr. 19, 2012

(30) Foreign Application Priority Data
May 5, 2008 (EP) .................................. 08155648

(51) Int. Cl.
*A61K 9/70* (2006.01)
(52) U.S. Cl.
CPC .............. *A61K 9/70* (2013.01); *A61K 9/7084* (2013.01)
(58) Field of Classification Search
CPC .................. A61K 9/70; A61K 9/7084
See application file for complete search history.

(56) References Cited

U.S. PATENT DOCUMENTS

| 5,866,164 | A * | 2/1999 | Kuczynski et al. ........... 424/472 |
| 6,685,956 | B2 * | 2/2004 | Chu ..................... A61K 9/0024 424/423 |
| 6,787,149 | B1 | 9/2004 | El Khoury et al. |
| 2002/0014307 | A1 | 2/2002 | Hidaka et al. |
| 2003/0068371 | A1 | 4/2003 | Oshlack et al. |
| 2005/0008776 | A1* | 1/2005 | Chhabra ........... A61F 13/15577 427/180 |
| 2005/0232982 | A1 | 10/2005 | Ihara et al. |
| 2006/0034900 | A1 | 2/2006 | Saeki et al. |
| 2011/0159076 | A1 | 6/2011 | Hoffmann et al. |
| 2011/0250256 | A1* | 10/2011 | Hyun-Oh et al. ............. 424/439 |

FOREIGN PATENT DOCUMENTS

| EP | 0 413 034 A1 | 2/1991 |
| EP | 0 484 543 A1 | 5/1992 |
| EP | 1 642 579 A1 | 4/2006 |
| JP | 3-163014 A | 7/1991 |
| JP | 2505674 B2 | 6/1996 |
| JP | 2003-277255 A | 10/2003 |
| JP | 2005-2009 A | 1/2005 |
| JP | 2006-76994 A | 3/2006 |
| WO | WO 91/16044 A1 | 10/1991 |
| WO | WO 2006/099541 A2 | 9/2006 |
| WO | WO 2007/137732 A2 | 12/2007 |
| WO | WO 2009/135846 A1 | 11/2009 |

OTHER PUBLICATIONS

Ramachandran et al., Drug Development and Industry Pharmacy, 25(2), 153-161 (1999).*
Yoo et al., Korea-Australia Rheology Journal, 25(2), 67-75, May 2013.*
Ohmori et al., CNS Drug Review vol. 8, No. 4, pp. 391-404.*
P.H. Stahl et al., Chem. Intl., 2002, vol. 24, No. 3.*
Wikipedia page from http://en.wikipedia.org/wiki/Pyoderma_gangrenosum (printed Jan. 20, 2015).*
Flock, P., "Pilot Study to Determine the Effectiveness of Diamorphine Gel to Control Pressure Ulcer Pain," *J. Pain Symptom Manage* 25:547-554, Elsevier Inc., United States (2003).
Hasirci, V., et al., "Antihyperalgesic effect of simultaneously released hydromorphone and bupivacaine from polymer fibers in the rat chronic constriction injury model," *Life Sci.* 73:3323-3337, Elsevier Inc., Netherlands (2003).
Kang, X.-J., et al., "Performance of electrospun nanofibers for SPE of drugs from aqueous solutions," *J. Sep. Sci.* 31:3272-3278, Wiley-VCH, Germany (2008).
Krajnik, M. and Zylicz, Z., "Topical morphine for cutaneous cancer pain," *Palliat. Med.* 11:325-326, Sage Publications, England (1997).
Krajnik, et al., "Potential uses of topical opioids in palliative care—report of 6 cases," *Pain* 80:121-125, Elsevier Science B.V., Netherlands (1999).
Long, T.D., et al. "Morphine-Infused Silver Sulfadiazine (MISS) Cream for Burn Analgesia: A Pilot Study," *J. Burn Care Rehabil.* 22:118-123, The American Burn Association, United States (2001).
Luong-Van, E., et al., "Controlled release of heparin from poly(ε-caprolactone) electrospun fibers," *Biomaterials* 27:2042-2050, Elsevier Ltd., England (2006).
Twillman, R.K., et al. "Treatment of Painful Skin Ulcers with Topical Opioids," *J. Pain Symptom Manage* 17:288-292, Elsevier, United States (1999).

(Continued)

*Primary Examiner* — Robert Cabral
(74) *Attorney, Agent, or Firm* — Sterne, Kessler, Goldstein & Fox P.L.L.C.

(57) ABSTRACT

The present invention relates to a composition, comprising (i) a matrix made of polymeric nanofibers, and (ii) an opioid agonist within the matrix.

33 Claims, No Drawings

(56) References Cited

OTHER PUBLICATIONS

Verreck, G. et al., "Incorporation of drugs in an amorphous state into electrospun nanofibers composed of a water-insoluble, nonbiodegradable polymer," *J. Control. Release* 92:349-360, Elsevier B.V., Netherlands (2003).

Verreck, G., et al., "Preparation and Characterization of Nanofibers Containing Amorphous Drug Dispersions Generated by Electrostatic Spinning," *Pharm. Res.* 20:810-817, Plenum Publishing Corporation, United States (2003).

Wang, X., et al., "Formation of water-resistant hyaluronic acid nanofibers by blowing-assisted electro-spinning and non-toxic post treatments," *Polymer* 46:4853-4867, Elsevier Ltd., England (2005).

Watterson, G. et al., "Peripheral opioids in inflammatory pain," *Arch. Dis. Child* 89:679-681, British Medical Association, England (2004).

Welling, A., "A randomised controlled trial to test the analgesic efficacy of topical morphine on minor superficial and partial thickness burns in accident and emergency departments," *Emerg. Med. J.* 24:408-412, BMJ Publishing Group, England (2007).

Zeng, J., et al., "Influence of the drug compatibility with polymer solution on the release kinetics of electrospun fiber formulation," *J. Control Release* 105:43-51, Elsevier B.V., Netherlands (2005).

Zeppetella, G., et al., "Analgesic Efficacy of Morphine Applied Topically to Painful Ulcers," *J. Pain Symptom Manage.* 25:555-558, Elsevier, United States (2003).

International Search Report for International Application No. PCT/EP2009/055422, European Patent Office, Rijswijk, Netherlands, dated Feb. 10, 2009.

Unverified machine English language translation of Japanese Patent Publication No. JP 2003-277255 A (listed as document FP9 on accompanying form PTO/SB/08A).

\* cited by examiner

OPIOID COMPOSITION FOR TREATING SKIN LESIONS

FIELD OF THE INVENTION

The present invention relates to an opioid composition, which is useful for topical administration, in particular topical treatment of skin lesions.

BACKGROUND OF THE INVENTION

Opioid agonists relieve pain by acting on receptors in the central nervous system. However, systemically acting opioids have a number of side effects such as sedation, respiratory depression, nausea, and constipation. An alternative approach to pain control is to apply topically acting drugs to the peripheral site of origin of the pain. Topical drugs used to control pain will act locally on damaged or dysfunctional soft tissues or peripheral nerves. Topical delivery systems differ from transdermal delivery systems in that they target a site immediately adjacent to the site of delivery rather than using the skin as an alternate systemic delivery system. Their actions may be on the inflammatory response itself or on sensory neurons.

Opioids bind to specific opioid receptors in the central nervous system. There are three principal classes of opioid receptors, i.e. $\mu$, $\kappa$ and $\delta$ opioid receptors. These opioid receptors are usually not found in normal tissue and hence topical administration of opioids has not been discussed intensively.

U.S. Pat. No. 6,787,149, which is one of the few reports on topical opioid application, discloses a pharmaceutical composition which comprises an admixture of an opioid agonist agent and a pharmaceutically acceptable excipient for topical administration to inflamed skin or mucosal tissue. Topical excipients listed in U.S. Pat. No. 6,787,149 comprise creams, ointments, gels or petrolatum.

G. Watterson et al., *Arch. Dis. Child.*, 2004, 679-681, disclose the use of topical morphine gel in the treatment of children with epidermolysis bullosa, where acute inflammatory pain is a major symptom.

A. Welling, *Emerg. Med. J.*, 2007, 408-412, discusses the agonist efficacy of topical morphine on superficial burns. A gel comprising morphine sulfate was administered.

Skin lesions, e.g. resulting from burns or ulcers, may cover larger skin areas. However, the larger the wound area that needs topical treatment, the higher is the risk of systemic absorption. Thus, for the treatment of skin lesions, in particular those covering a larger skin area, there is a continuing need for pharmaceutical compositions that allow topical treatment and at the same time prevent systemic absorption as much as possible.

SUMMARY OF THE INVENTION

It is an object of the present invention to provide an opioid composition useful for the topical treatment of skin lesions, in particular those covering larger skin areas, which is not substantially systemically absorbed but still provides the desired analgesic effect.

This objective, as well as others, which will become apparent from the ensuing description, is attained by the subject matter of the independent claims. Some of the preferred embodiments of the present invention are defined by the dependent claims. In one embodiment the present invention relates to a pharmaceutical composition, comprising a matrix made of polymeric fibers, and
at least one opioid agonist and/or at least one pharmaceutically acceptable salt thereof.

Typically said matrix may be a non-woven matrix. The at least one opioid agonist and/or pharmaceutically acceptable salt thereof may be comprised within the matrix.

In a preferred embodiment such matrices can be made from nanofibers.

Such nanofibers may be made from biodegradable or non-biodegradable polymers and polymers with wound healing capability. In one embodiment the nanofibers may have an average fiber diameter in the range of from about 10 nm to about 500 nm.

One of the preferred embodiments relates to a pharmaceutical dosage form comprising a matrix in the form of a non-woven mat made from nanofibers comprising at least one opioid agonist and/or a pharmaceutically acceptable salt thereof.

In one embodiment the pharmaceutical dosage form comprises opioids and/or pharmaceutically acceptable salts thereof that are preferably selected from the group comprising morphine, morphine-6-glucuronide, buprenorphine, oxycodone, hydromorphone, oxymorphone, fentanyl, sufentanil, alfentanil, remifentanil, propoxyphene, nicomorphine, dihydrocodeine, diamorphine, papaveretum, codeine, ethylmorphine, phenylpiperidine, methadone, dextropropoxyphene, buprenorphine, pentazocin, tilidine, tramadol, hydrocodone, loperamide, or any combination thereof. Preferred opioids are morphine, buprenorphine, hydromorphone, oxycodone, oxymorphone, fentanyl and loperamide.

In another preferred embodiment, the pharmaceutical dosage form comprises opioids and/or pharmaceutically acceptable salts thereof that are known to preferentially act as $\mu$ and/or $\delta$ opioid receptor agonists. Such opioids include norbuprenorphine, etorphine, dihydroetorphine, as well as the peptides leu-enkephalin/met-enkephalin and their derivatives, and $\beta$-endorphin and its derivatives.

In a preferred embodiment the pharmaceutical compositions in accordance with the invention will be designed to provide controlled release of the opioid(s) and/or pharmaceutically acceptable salts thereof. In a preferred embodiment the pharmaceutical dosage forms will provide zero order release kinetics.

The amount of the opioid(s) and/or pharmaceutically acceptable salts thereof will depend on the respective active agent. However, the invention preferably relates to pharmaceutical compositions, which comprise an amount of an opioid and/or a pharmaceutically acceptable salt thereof sufficient to achieve topical efficacy and for which the release characteristics are adjusted to not allow systemic absorption or only of a minimum without a significant systemic impact. In a further preferred embodiment the amount of opioid and/or a pharmaceutically acceptable salt thereof and the release characteristics will be chosen such that a therapeutic efficacy is achieved for at least 12 hours, preferably for at least 24 hours, for at least 36 hours, for at least 48 hours, for at least 72 hours or even longer, such as for 5, 6 or 7 days.

The person skilled in the art will realize that in case where the pharmaceutical dosage form is a transdermal dosage form such as a patch, it may take different shapes and dimensions. Thus, the dosage form may be round, elliptical, rectangular, square etc.

In one embodiment the pharmaceutical composition may be designed to allow covering a surface area of a few $cm^2$ upon topical application. The size and dimensions of the dosage form will typically depend on the area that needs to be covered. Typically, the pharmaceutical compositions may allow a surface area of 1×2 cm, of 2×4 cm, of 5×10 cm, of 10×20 cm, of 10×40 cm or 20×40 cm to be covered. If the dosage form is round, its diameter may be e.g. 1 cm, 2 cm, 5 cm, 10 cm, 20 cm and up to 40 cm. If e.g. a leg ulcer is to be treated the dosage form may allow a surface area of 1×1 cm, of 2×2 cm, of 5×5 cm, of 10×10 cm, of 20×20 cm and up to 40×40 cm to be covered.

According to one aspect a large non-woven sheet can be made which can be cut later to a size appropriate to suit the needs of the patient. Further, the dosage form may be a patch where areas with active agent are surrounded by and/or separated from each other by borders that are free of active agent. These borders may have dimensions of e.g. 3 mm to 3 cm. These borders may allow batches of defined dosage amounts to be separated by e.g. cutting and help to avoid that one cuts into the drug-containing part of the patch. Of course, the borders may contain means to further ease separation of dosage form such as perforation lines. The borders may also have adhesive properties allowing fixation of the pharmaceutical dosage form to the patient's skin.

In one embodiment the pharmaceutical composition may take the form of a patch, a wound dressing or a gauze.

The pharmaceutical composition may be used for topical treatment of skin lesions, preferably open skin lesions. Such skin lesions can result from ulcers, preferably decubitus ulcers, diabetic ulcers, leg ulcers, pressure ulcers, from skin graft donor sites, or from burns. The pharmaceutical compositions may preferably be used for treating symptoms that result from the afore-mentioned ulcers including e.g. pain provoked by these ulcers. The topical treatment of leg ulcers and preferably venous leg ulcer or chronic leg ulcer is particularly considered with the pharmaceutical compositions of the present invention. The pharmaceutical compositions may also be used for assisting topical wound healing of the afore-mentioned ulcers.

Another embodiment of the present invention relates to the use of the afore-mentioned pharmaceutical compositions in the manufacture of a medicament for topically treating skin lesions and ulcers or symptoms such as pain resulting from the aforementioned skin lesions and ulcers. The present invention also relates to the use of the afore-mentioned pharmaceutical compositions in the manufacture of a medicament for topically assisting wound healing of the above-mentioned skin lesions and ulcers.

Yet another embodiment of the present invention relates to a method of topically treating skin lesions and ulcers or symptoms such as pain resulting from the aforementioned skin lesions and ulcers by administering to a human or animal being pharmaceutical compositions as described above. Methods of topically assisting wound healing by administering the afore-mentioned pharmaceutical dosage forms also forms part of the invention.

Yet another embodiment of the present invention relates to methods of producing the afore-mentioned pharmaceutical compositions. Such methods may e.g. include electrospinning polymeric (nano)fibers into a non-woven matrix. Opioids and/or pharmaceutically acceptable salts thereof may be incorporated either during or after producing the matrix from polymeric (nano)fiber.

DETAILED DESCRIPTION OF THE INVENTION

The inventors of the present invention have surprisingly found that using a matrix which is made from polymeric fibers can be used to produce a pharmaceutical composition which releases an opioid or a pharmaceutically acceptable salt thereof in a controlled manner.

This controlled release will provide the desired analgesic effect by local action and without substantial and preferably without any detectable systemic absorption, even if topical administration over a large wound area and over extended periods of time is necessary.

Before some of the embodiments of the present invention are described in more detail, the following definitions are introduced.

As used in this specification and in the appended claims, the singular forms of "a" and "an" also include the respective plurals unless the context clearly dictates otherwise. Thus, the term "an opioid agonist" can include more than one agonist, namely two, three, four, five etc. opioid agonists.

The terms "about" or "approximately" in the context of the present invention denotes an interval of accuracy that the person skilled in the art will understand to still ensure the technical effect of the feature in question. The term typically indicates deviation from the indicated numerical value of +/−10%, and preferably +/−5%.

It is to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to disclose a group, which preferably consists only of these embodiments.

When it is mentioned that the dosage forms in accordance with the invention substantially do not allow for synthetic absorption, this means that the extent of systemic absorption does not lead to significant side effects and/or preferably is below and/or approximately equal to the minimum effective blood plasma concentration known for the respective agent.

Further definitions of terms will be given in the context in which the terms are used.

As mentioned, in one embodiment the present invention relates to a pharmaceutical composition, comprising
 a matrix made of polymeric fibers, and
 at least one opioid agonist and/or at least one pharmaceutically acceptable salt thereof.

Typically said matrix may be a non-woven matrix. The at least one opioid agonist and/or at least one pharmaceutically acceptable salt thereof may be comprised within the matrix.

The matrix can preferably be made from polymeric nanofibers.

Such matrix systems allow for controlled release of the at least one opioid agonist and/or at least one pharmaceutically acceptable salt thereof.

In the context of the present invention, controlled release means that the pharmaceutically active agent(s) is (are) released over an extended period of time. Typically, the release of the active agent(s) contained within the pharmaceutical composition will take place over at least about 4 h, over at least about 8 h and preferably over at least about 12 h, at least about 24 h, at least about 36 h or at least about 48 h, at least about 72 h or even longer such as for 4, 5 6 or 7 days. The drug release is measured by methods known in the art for topical and preferably transdermal dosage forms. One approach may be to use the Basket Method of the European Pharmacopoeia. While the basket method is usually applied for oral dosage forms, one may take a piece of the pharmaceutical dosage form in accordance with the invention and test the release of active from this piece following the procedure of the basket method. The actual release rate may then be indicated as %-release (active)/cm$^2$ of piece tested.

Preferably, the pharmaceutical compositions allow for first order release kinetics and more preferably for zero order release kinetics.

In the context of the present invention, the term "opioid agonist" is used as known in the art. For the purposes of the present invention it will be considered to be equivalent to the term "opioid analgesic". Typically, a pharmaceutically active agent will be considered to be an opioid agonist if it belongs to Class NO2A of opioid agonists according to the Anatomical Therapeutic Chemical classification (ATC classification) of the World Health Organization (WHO).

Opioid agonists which can be used in the context of the present invention include morphine, morphine-6-glucuronide, oxycodone, hydromorphone, propoxyphene, nicomorphine, dihydrocodeine, diamorphine, papaveretum, codeine, ethylmorphine, phenylpiperidine and derivates thereof, methadone, dextro-propoxyphene, buprenorphine, norbuprenorphine, pentazocine, tilidine, etorphine, dihydroetorphine, tramadol, hydrocodone, loperamide, fentanyl, sufentanil, alfentanil, remifentanil, and the peptides leu-enkephalin and met-enkephalin and β-endorphin including all their derivatives. Further examples for useable agonists according to the invention are meperidine, oxymorphone, alphaprodine, anileridine, dextromoramide, metopone, levorphanol, phenazocine, etoheptazine, propiram, profadol, phenampromide, thiambuten, pholcodeine, codeine, dihydrocodeinon, fentanyl, 3-trans-dimethylamino-4-phenyl-4-trans-carbethoxy-$\Lambda'$-cyclohexen, 3-dimethylamino-0-(4-methoxyphenyl-carbamoyl)-propiophenone oxime, (-)13-2'-hydroxy-2,9-dimethyl-5-phenyl-6,7-benzomorphane, (-)2'-hydroxy-2-(3-methyl-2-butenyl)-9-methyl-5-phenyl-6,7-benzomorphane, pirinitramide, (-)α-5,9-diethyl-2' hydroxy-2-methyl-6,7-benzomorphane, ethyl 1-(2-dimethylaminoethyl)-4,5,6,7-tetrahydro-3-methyl-4-oxo-6-phenyl-indol-2-carboxylate, 1-benzoylmethyl-2,3-dimethyl-3-(m-hydroxy-phenyl)-piperidine, N-allyl-7α(1-R-hydroxy-1-methylbutyl)-6,14-endo-ethanotetrahydronororipavine, (-)2'-hydroxy-2-methyl-6,7-benzomorphane, noracylmethadol, phenoperidine, α-d1-methadol, α-1-methadol, β-d1-acetylmethadol, α-1-acetylmethadol and β-1-acetylmethadol or combinations thereof.

In a preferred embodiment, the opioid agonist is selected from the group consisting of morphine, oxycodone, hydromorphone, oxymorphone, propoxyphene, nicomorphine, dihydrocodeine, diamorphine, papaveretum, codeine, ethylmorphine, phenylpiperidine, methadone, dextropropoxyphene, buprenorphine, pentazocin, tilidine, tramadol, hydrocodone, loperamide, fentanyl, sufentanil, alfentanil, remifentanil, and the peptides enkephalin and endorphin including their derivatives and any combination thereof.

Particularly interesting opioids are morphine, hydromorphone, buprenorphine, norbuprenorphine and dihydroetorphine.

Preferably, the opioid agonist has a binding affinity to the δ opioid receptor or the μ and δ opioid receptor. Such opioids are for example norbuprenorphine, etorphine, dihydroetorphine, and the peptides leu-enkephalin, met-enkephalin and β-endorphin including their derivatives.

Loperamide acts on the μ-opioid receptors. However, it does not affect the central nervous system like other opioids. Thus, to further reduce the risk of potential systemic side effects, peripherally acting opioid receptor agonists such as loperamide might be preferred. In other embodiments of the present invention, the opioid agonist, which is present within the nanofiber matrix, may not be loperamide.

Preferably, the opioid agonist is present in the form of a pharmaceutically acceptable salt, preferably as the hydrochloride, sulfate, bisulfate, tartrate, nitrate, citrate, bitartrate, phosphate, malate, maleate, hydrobromide, hydroiodide, fumarate or succinate salt.

The amount of the at least one opioid agonist and/or at least one pharmaceutically acceptable salt thereof is chosen such that, in combination with the release properties, a therapeutic efficacy is achieved over at least about 8 h and preferably over at least about 12 h, over at least about 24 h, over at least about 36 h or preferably over at least about 48 h, over at least about 72 h or longer upon topical application. The controlled release properties, i.e. the release rate from the pharmaceutical composition should be chosen to allow for minimum absorption without a significant systemic action.

The person skilled in the art is capable of identifying an amount and release rates for a specific opioid agonist and/or a pharmaceutically acceptable salt thereof that do not lead to substantial systemic absorption. As a first estimate, one may rely on knowledge from oral dosage forms for which a relationship between the amount of opioid agonist (or of its salt), the in vitro release data and in vivo blood plasma levels has been established. Starting from such data, one may use the minimal blood plasma levels required for systemic therapeutic efficacy to determine the allowed mean maximum blood plasma concentration for the pharmaceutical dosage forms of the present invention. Based thereon and on the release data achieved by the pharmaceutical compositions in accordance with the invention, the amount and optionally the in vitro release data of the at least one opioid and/or salt thereof can be established.

In case of morphine the amount and/or in vitro release rates should be chosen such that upon topical administration the mean maximum plasma concentration of morphine is less than 8 ng/ml, more preferably less than 4 ng/ml, even more preferably less than 2 ng/ml after topical administration. In the case of morphine, one may use up to 10 mg morphine and/or an equivalent amount of a pharmaceutically acceptable salt thereof such as morphine sulphate for treating an area of from about 50 to about 100 cm$^2$ for up to 24 hours or even longer.

Preferably, the mean maximum plasma concentration of hydromorphone is less than 4 ng/ml, more preferably less than 2 ng/ml, even more preferably less than 0.5 ng/ml after topical administration.

Preferably, the mean maximum plasma concentration of buprenorphine is less than 400 pg/ml, more preferably less than 200 pg/ml, even more preferably less than 100 pg/ml after topical administration.

Preferably, the mean maximum plasma concentration of fentanyl is less than 800 pg/ml, more preferably less than 400 pg/ml, even more preferably less than 200 pg/ml after topical administration.

The person skilled in the art is familiar with measuring such pharmacokinetic parameters. Typically one will measure pharmacokinetic parameters for approximately 12 to 24 healthy human beings and calculate the average to obtain mean values. Healthy human subjects are selected as suggested by ICH (International Conference on Harmonisation on Good Clinical Practice) and as implemented by the EMEA and/or FDA. Thus the skilled person will follow inclusion and exclusion criteria as they are common for clinical phase I trials of controlled release preparations of opioid analgesics. The healthy human beings may preferably be of Caucasian origin and have average weight, size, height etc.

In a preferred embodiment, the upper limits of the mean maximum plasma concentration indicated above are still not exceeded even though topical administration is effected over a skin surface area within the range of 0.1 cm² to 1000 cm² of 1 cm² to 400 cm², of 1 cm² to 200 cm², of 1 to 100 cm² or 1 to 50 cm².

Another approach for identifying the amount of opioid for the pharmaceutical composition of the present invention is to take those amounts, which have been used for topical opioid formulations in the art as a guiding parameter. Thus, morphine gel formulations have been used with Intrasite gel (Smith & Nephew) (see reference of Krajnik et al. and Zeppetalla et al., *Flock J Pain Sympt Manage* 2003, 25:547-554, Twillmann et al., *J Pain Sympt Manage* 1999, 17:288-292) and silver sulfadiazine (e.g. Flamazine; Smith & Nephew) (Long et al, *J Burn Care Rehabil* 2001, 22:118-123).

Preferably, the opioid agonist and/or an equivalent amount of a pharmaceutically acceptable salt thereof is present in an amount of from 0.01 mg/g composition to 100 mg/g composition, more preferably from 0.05 mg/g composition to 50 mg/g composition, even more preferably from 0.1 mg/g composition to 20 mg/g composition.

By keeping the mean maximum plasma concentration of the opioid agonist (or salt) below the value indicated above and/or the amount of opioid agonist (or salt) within the above indicated ranges, systemic absorption is effectively suppressed. Thus, the composition is acting mainly topically.

Other pharmacologically active agents such as antiseptic, antibiotic antifungal antiviral agents can be added to reduce secondary bacterial fungal and viral infection. Combinations with local anaesthetic agents may further improve analgesic action.

An appropriate release rate of the opioid agonist from the dosage forms can be accomplished by selecting an appropriate polymeric fiber material and/or an appropriate amount of opioid agonist (or salt) e.g. within the matrix, as will be described in further detail below. The use of nanofibers can be preferred.

Preferably, the polymeric (nano)fibers are present in the form of a non-woven mat. The mat is formed by entanglement of randomly oriented fibers. However, it is also possible to introduce some degree of fiber orientation, e.g. by post-treatment steps.

Nanofibers are preferred. The nanofibers can have an average diameter in the range of from about 10 to about 500 nm and preferably in the range of from about 20 to about 400 or from about 30 to about 300 nm. The diameter can be determined by e.g. scanning electron microscopy.

The polymeric (nano)fibers can be made from polymers of biological origin or from synthetic polymers.

Moreover, the polymers can be biodegradable with or without wound healing properties. Within the context of the present invention, the term "biodegradable polymer" refers to a polymer being degradable by the action of naturally occurring microorganisms such as bacteria, fungi, and algae. The term also refers to polymers that degrade over time by natural hydrolysis, oxidation and other means. However, such polymers should not be prone to degradation during the time course of application, which is typically in the range of 1 to 7 days, unless (otherwise) the degradation process is used to enhance the drug release from the non-woven mat.

Preferably, at least some of the polymeric nanofibers are made of biodegradable polymers.

Preferably, the biodegradable polymer for (nano)fiber production is selected from the group comprising poly (lactic acid), poly (glycolic acid), poly (lactic-co-glycolic acid), poly (ε-caprolactone), polyvinyl-caprolactame (PVCL), polyhydroxyalkanoates, poly(-caprolactone)-systems, poly (alkylene succinates), poly(ethylene/butylenessuccinate), poly(ethylene/butylene adipate), poly (β-hydroxybutrate-co-β-hydroxyvalcratc), hyaluronic acid, agarose, dextrose, cellulose, starch, chitin, gelatine, or any mixture thereof.

Preferably, at least some of the polymeric nanofibers are made of a non-biodegradable polymer.

Preferably, the non-biodegradable polymer is selected from the group comprising poly(ethylene-co-vinyl acetate), polyvinyl acetate, polyvinyl pyrrolidone, polyurethane, or polyethylene terephthalate.

Within the present invention, it is possible to use the biodegradable polymer and the non-biodegradable polymer, respectively, only. However, it is also possible to use a combination of these for the preparation of the polymeric nanofibers.

Preferably, the polymeric nanofibers are prepared by electrospinning

In general, electrospinning is a well-established method for producing nanofibers. The electrospinning process uses high voltage to create an electric field between a droplet of melted polymer or polymer solution at the tip of a needle and a collector plate. One electrode of the voltage source is placed into the method polymer or polymer solution and the other is connected to the collector. This creates an electrostatic force. As the voltage is increased, the electric field intensifies causing a force to build up on the pendant drop of melted polymer or polymer solution at the tip of the needle. This force acts in a direction opposing the surface tension of the drop. The increasing electrostatic force causes the drop to elongate forming a conical shape known as the Taylor cone. When the electrostatic force overcomes the surface tension of the drop, a charged continuous jet of melted polymer or polymer solution is ejected from the cone. The jet accelerates towards the collector. As it moves away from the needle and toward the collector, the jet rapidly thins and dries (in the case of the solution) as the solvent evaporates. On the surface of the collector, a non-woven mat of randomly oriented solid nanofibers is deposited.

There are also publications relating to the use of electrospun nanofibers in healthcare applications.

E. Luong-Van et al., *Biomaterials*, Vol. 27, 2042-2050, 2005, prepared nanofibers from heparin-loaded poly (caprolactone) solution in dichloromethane/methanol.

J. Zeng et al., *Journal of controlled release*, Vol. 105, 43-51, 2005, studied electrospun fibers of anticancer drugs paclitaxel, doxorubicin hydrochloride and doxorubicin base.

G. Verreck et al., *Pharmaceutical research*, Vol. 20, 810-817, 2003, studied the application of water-soluble polymer-based nanofibers prepared by electrospinning Organic solvent-based solutions of itraconazole/HPMC mixture were electrospun at 16 and 24 kV. The formed nanofibers were collected as a non-woven mat.

X. Wang et al., *Polymer*, 46, 4853-4867, 2005, disclose a method of electrospinning hyaluronic acid nanofibers using controlled temperature air blowing to improve processing and enhance drying.

With regard to appropriate process parameters for electrospinning, reference is made to the documents cited above.

In a preferred embodiment, the matrix, preferably the non-woven mat of nanofibers, has a controllable specific surface area and/or a porosity to modulate the drug release rate and profile.

Preferably, electrospinning of the nanofibers is carried out in the presence of the opioid agonist. In a preferred embodiment, the opioid agonist is added to the polymer, preferably a polymer solution, prior to the electrospinning step. However, in an alternative, it is possible to load the opioid agonist to the matrix, preferably the non-woven mat, after electrospinning.

If electrospinning is carried out in the presence of the opioid agonist, it may be at least partially distributed within the inner part or bulk part of the electrospun polymer. If applied after the electrospinning step, the opioid at least partially covers the nanofiber surface.

The polymer can be electrospun from a solvent or neat (i.e. as a melt).

In a preferred embodiment, the polymer is electrospun from a solvent or a mixture of at least two solvents. Preferably, the solution comprises the opioid agonist as well. Appropriate solvents that could be mentioned here include water, alcohols ketones, and dichloromethane.

It is also possible to add additives such as plasticizers, release rate modifiers to the polymeric solution prior to the electrospinning step.

The pharmaceutical composition may comprise other compounds besides the matrix. Thus, the pharmaceutical composition may comprise e.g. a phase that releases the opioid agonist and/or a pharmaceutically acceptable salt thereof in an immediate manner to provide a rapid onset of action. This immediate release phase may e.g. be an active comprising coating that is disposed on the matrix. The immediate release phase has, of course, been selected such that systemic absorption is avoided.

The pharmaceutical composition may also comprise a coating that does not add immediate release properties to the composition but helps to fine tune the controlled release characteristics of the composition.

Optionally, the composition comprises one or more pharmaceutically acceptable excipients. These excipients may be selected to convey additional beneficial characteristics to the composition. For example, the composition may comprise preservatives, stabilizers, antioxidants, dyes etc.

Although the nanofibers inherit tamper resistance properties to the pharmaceutical compositions of the present invention due to the very slow drug release rate and low drug load, the composition may likewise comprise excipients that render the pharmaceutical composition at least partially tamper resistant. Thus, the opioid-comprising matrix may additionally contain a gel former. Such gel formers lead to a formation of a gel upon contacting the matrix with fluids such as water, buffers or organic solvent including alcohol. This may make it harder for a person to extract the opioid agonist from the composition and to draw it into a syringe for illicit intravenous injection.

The pharmaceutical composition may be provided in different forms. A sterile patch, a wound dressing, or a gauze can be preferred.

According to another aspect, the present invention provides a composition as defined above for the topical treatment of skin lesions, preferably open skin lesions.

The skin lesions can result from ulcers, preferably decubitus ulcers, diabetic ulcers, leg ulcers, pressure ulcers, from skin graft donor sites, or from burns.

Decubitus ulcers, also known as bed sores or pressure sores, develop when the blood supply to a person's skin is cut off as a result of prolonged pressure caused by extended periods of time spent without movement. People in wheel chairs and those who are bedridden due to injury or illness are most prone to develop decubitus ulcers. It is estimated that approximately one million people will develop a decubitus ulcer each year in the United States. Sixty thousand Americans die from the complications of more advanced decubitus ulcer stages every year.

Diabetic ulcers, in particular diabetic foot ulcers, occur as a result of various factors. Such factors include mechanical changes in conformation of the bony architecture of the foot, peripheral neuropathy, and atherosclerotic peripheral arterial disease, all of which occur with higher frequency and intensity in the diabetic population. Non-enzymatic glycosylation predisposes ligaments to stiffness. Neuropathy causes loss of protective sensation and loss of coordination of muscle groups in the foot and leg, both of which increase mechanical stresses during ambulation.

Preferably, the leg ulcers are venous leg ulcer or chronic leg ulcer.

A venous leg ulcer is an open sore in the skin of the lower leg due to high pressure of the blood in the leg veins. The main cause of venous leg ulcers is faulty valves inside the leg veins. These valves normally allow the blood to flow up the leg towards the heart, and prevent backward flow down the leg. If they are faulty, backward flow is not prevented and pressure builds up inside the veins. The persistent high-pressure in the leg veins, caused by the faulty valves, damages tiny blood vessels in the skin. The skin then becomes thin and inflamed, does not heal well, and can easily break down to leave an open sore, otherwise known as an ulcer.

Preferably, the topical treatment includes treatment of pain or other symptoms, which result from skin lesions.

Preferably, the topical treatment of the skin lesion with the composition of the present invention also promotes wound healing of skin lesions. Thus, in addition to pain management, the composition of the present invention can also be used to improve the healing process of skin lesions.

According to another aspect, the present invention provides the use of the composition as defined above for the preparation of a medicament for the topical treatment of skin lesions, preferably open skin lesions.

The invention has been illustrated with respect to some of its preferred embodiments. The person skilled in the art is, however, clearly aware of other embodiments that also lie within the scope of the invention. The above embodiments are therefore not to be understood as limiting.

The invention claimed is:

1. A pharmaceutical composition, comprising
    (a) a polymeric nanofiber matrix, wherein. the nanofibers have an average diameter in the range of from about 10 to about 500 nm;
    (b) at least one pharmaceutically acceptable salt of an opioid agonist, wherein the opioid agonist is present in an amount of from 0.01 mg/g composition to 100 mg/g composition; and
    (c) an additional gel forming agent in solid form;
    wherein at least some of the polymeric nanofibers of (a) are made of a biodegradable polymer, wherein the biodegradable polymer is selected from the group consisting of poly (lactic acid), poly (glycolic acid), poly (lactic-co-glycolic acid), poly ($\epsilon$-caprolactone), polyvinyl-caprolactame (PVCL), polyhydroxyalkanoates, poly(-caprolactone) -systems, poly (alkylene succinate), poly(ethylene/butylene succinate), poly(ethylene/butylene adipate), poly ($\beta$-hydroxybutyrate-co-$\beta$-hydroxyvalerate), hyaluronic acid, agarose, cellulose, and any mixture thereof,
    wherein (b) and (c) are independently contained within and/or on the matrix, wherein the matrix provides a controlled release of said at least one pharmaceutically acceptable salt of the opioid agonist from the composition, wherein the gel forming agent, upon contacting the composition with a fluid, forms a gel, wherein said gel reduces extraction of the opioid agonist from the composition, and wherein the gel forming agent reduces the ability to extract the opioid agonist from the composition and draw it into a syringe for intravenous injection.

2. The pharmaceutical composition of claim 1, wherein the matrix is a non-woven matrix of polymeric nanofibers.

3. The pharmaceutical composition of claim 1, wherein the polymeric nanofibers have an average fiber diameter in the range of from about 20 ran to about 200 nm.

4. The pharmaceutical composition of claim 1, wherein said at least one pharmaceutically acceptable salt of the opioid agonist is within the matrix made of polymeric nanofibers.

5. The pharmaceutical composition of claim 1, wherein the opioid agonist is selected from the group consisting of morphine, oxycodone, buprenorphine, hydromorphone, oxymorphone, propoxyphene, nicomorphine, dihydrocodeine, diamorphine, papaveretum, codeine, ethylmorphine, phenylpiperidine, methadone, dextropropoxyphene, buprenorphine, pentazocin, tilidine, etorphine, dihydroetorphine, tramadol, hydrocodone, loperamide, and any mixture thereof.

6. The pharmaceutical composition of claim 1, wherein the opioid agonist has a binding affinity to the μopioid receptor and/or to the δopioid receptor.

7. The pharmaceutical composition of claim 6, wherein the opioid agonist is selected from norbuprenorphine, etorphine, dihydroetorphine, leu-enkephalin and its derivatives, met-enkephalin and its derivatives, and β-endorphin and its derivatives.

8. The pharmaceutical composition of claim 1, wherein the release follows substantially zero order release kinetics.

9. The pharmaceutical composition of claim 1, wherein an amount of the pharmaceutically acceptable salt of the opioid agonist and a release rate thereof are chosen to achieve topical efficacy only and to not allow for any substantial systemic uptake of the pharmaceutically acceptable salt of the opioid agonist.

10. The pharmaceutical composition of claim 1, further comprising one or more additional pharmaceutically active compounds selected from the group consisting of antiseptic agents, antibiotic agents, antifungal agents, antiviral agents, and anaesthetics.

11. The pharmaceutical composition of claim 1, wherein the composition is designed to cover a skin surface area in the range of from 1 cm$^2$ to 1000cm$^2$.

12. The pharmaceutical composition of claim 1, further comprising one or more pharmaceutically acceptable excipients.

13. The pharmaceutical composition of claim 12, wherein said one or more pharmaceutically acceptable excipients comprise a plasticizer.

14. The pharmaceutical composition of claim 12, wherein said one or more pharmaceutically acceptable excipients comprise preservatives, antioxidants, and colorants.

15. The pharmaceutical composition of claim 1, wherein the composition is provided in the form of a patch, a wound dressing, or a gauze.

16. The composition of claim 1, wherein the said composition is used for topical treatment of skin lesions.

17. The composition of claim 16, wherein the skin lesions result from ulcers, from skin graft donor sites, or from burns.

18. The composition of claim 17, wherein the skin lesions result from a venous leg ulcer or chronic leg ulcer.

19. The composition of claim 16, wherein the topical treatment includes treatment of pain, which results from skin lesions.

20. The composition of claim 16, wherein the topical treatment promotes wound healing of skin lesions.

21. A method of topically treating skin lesions, comprising topically applying a composition of claim 1 to said skin lesions.

22. The method of treating of claim 21, wherein the skin lesions result from ulcers, from skin graft donor sites, or from burns.

23. The method of treating of claim 22, wherein the skin lesions result from decubitus ulcers, diabetic ulcers, leg ulcers, or pressure ulcers.

24. The method of treating of claim 21, wherein the topical treatment includes treatment of pain which results from skin lesions.

25. The method of treating of claim 21, wherein the topical treatment promotes wound healing of skin lesions.

26. A process for producing the matrix of claim 1, comprising electrospinning polymeric nanofibers to form the matrix.

27. The process for producing the matrix of claim 26, comprising electrospinning the fibers in the presence of the at least one pharmaceutically acceptable salt of the opioid agonist.

28. The process for producing the matrix of claim 26, wherein the at least one pharmaceutically acceptable salt of the opioid agonist is added to the matrix after electrospinning.

29. The pharmaceutical composition of claim 1, wherein said at least one pharmaceutically acceptable salt of the opioid agonist is present in the form of a pharmaceutically acceptable hydrochloride, sulfate, bisulfate, tartrate, nitrate, citrate, bitartrate, phosphate, mutate, maleate, hydrobromide, hydroiodide, fumarase or succinate salt.

30. The composition of claim 16, wherein the composition is used for the topical treatment of open skin lesions.

31. The method of treating of claim 21, wherein the composition is topically applied to open skin lesions.

32. The method of treating of claim 23, wherein the leg ulcers are venous leg ulcer or chronic leg ulcer.

33. The pharmaceutical composition of claim 1, wherein the fluid is water, a buffer, or an organic solvent.

* * * * *